United States Patent [19]
Nelson

[11] Patent Number: 5,814,002
[45] Date of Patent: Sep. 29, 1998

[54] ADJUSTABLE SIZE ANKLE BRACE

[76] Inventor: Ronald E. Nelson, 1120 Second St., Box 441, Chetek, Wis. 54728

[21] Appl. No.: 848,898

[22] Filed: May 1, 1997

[51] Int. Cl.$^6$ .................................. A61F 5/00; A61F 5/37
[52] U.S. Cl. ............................... 602/27; 602/65; 128/882
[58] Field of Search ................... 602/23, 27, 62, 602/65; 128/882

[56] References Cited

U.S. PATENT DOCUMENTS

| | | | |
|---|---|---|---|
| 4,280,488 | 7/1981 | Polsky et al. | 602/27 |
| 4,513,740 | 4/1985 | Westlake | 602/62 |
| 4,527,556 | 7/1985 | Nelson . | |
| 4,651,726 | 3/1987 | Holland | 602/65 |
| 4,878,505 | 11/1989 | Thanner | 128/882 |
| 5,067,486 | 11/1991 | Hely | 602/27 |
| 5,657,767 | 8/1997 | Nelson et al. | 128/882 |

*Primary Examiner*—Richard J. Apley
*Assistant Examiner*—Denise Pothier
*Attorney, Agent, or Firm*—Burd, Bartz & Gutenkauf

[57] ABSTRACT

An adjustable size ankle brace that can be configured to be fitted on feet of differing sizes. The brace includes a base that wraps around the foot and ankle on the sides and rear thereof. The base has forward edges that come toward one another over the front superior foot and ankle region but do not meet. The edges are spaced apart by a gap that is closed by an adjustable closure assembly. Lateral and medial movable flaps are releasable fixed to the sides of the base by means of hook and loop type fastening material. The flaps carry lace eyelets. The eyelets are connected by a common lace. The flaps can be moved on the base to vary the circumference size encompassed by the base and accordingly the size of the brace.

17 Claims, 4 Drawing Sheets

FIG. 3

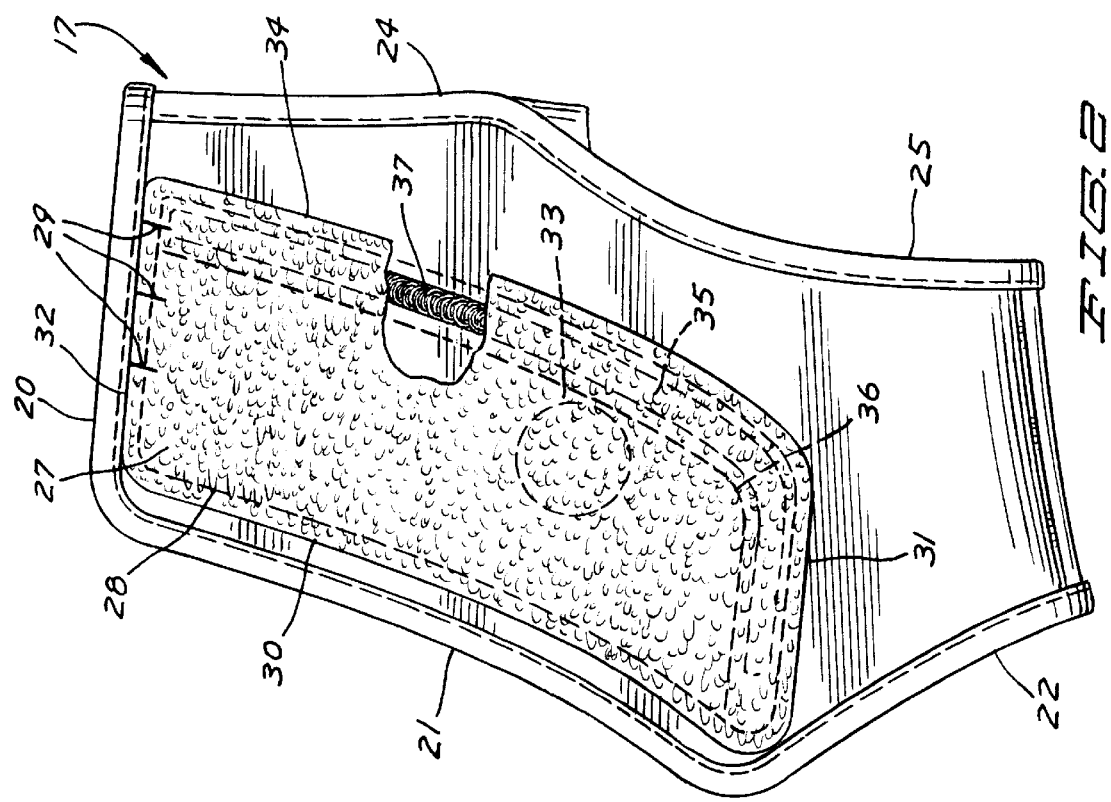

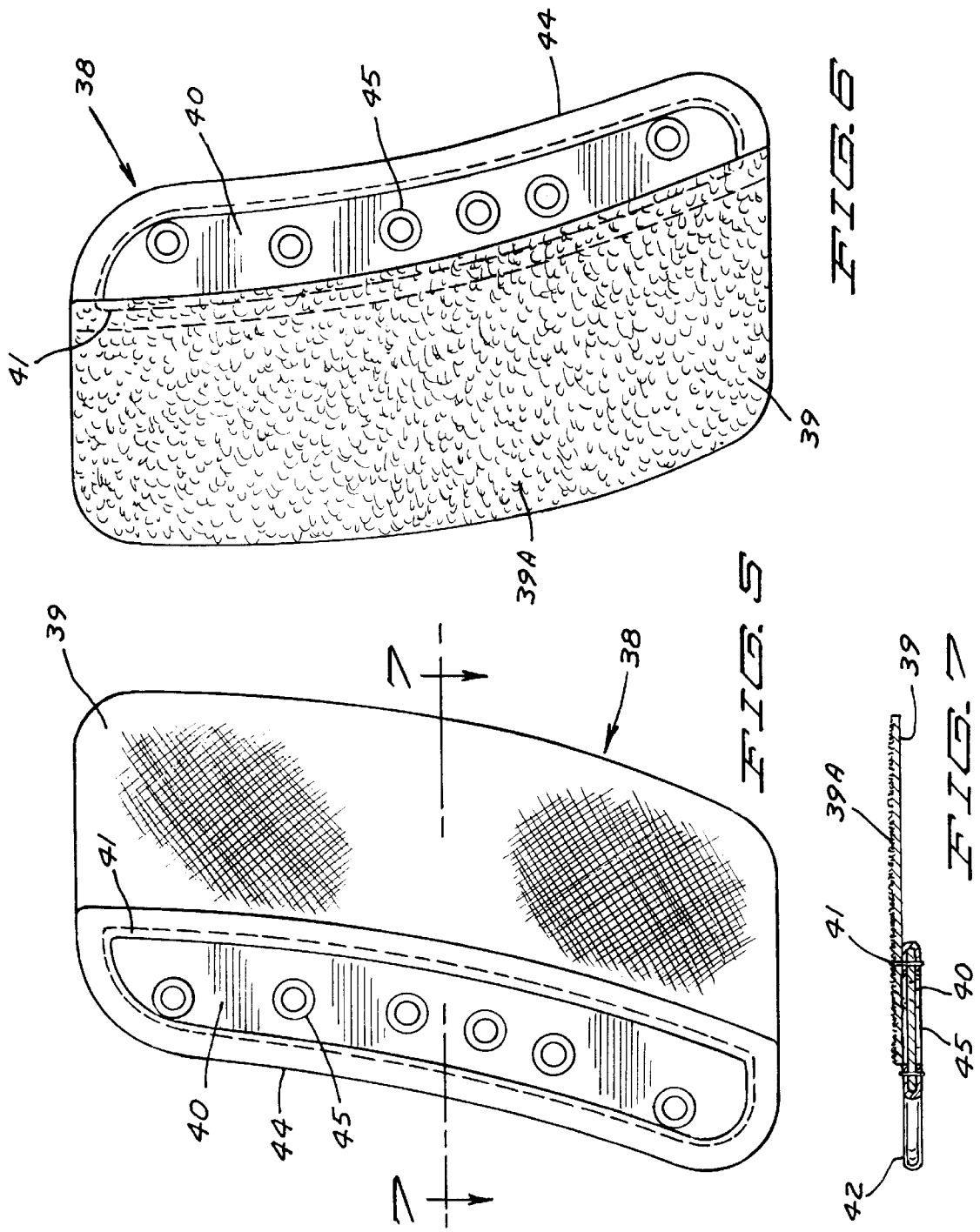

ADJUSTABLE SIZE ANKLE BRACE

BACKGROUND OF THE INVENTION

The ankle joint is very stable and resistant to injury. It is one of the most used and abused joints of the human body and consequently is frequently subject to injury, particularly upon participation in certain rugged sports. The ankle joint is the complex articulation joint of the fibula and tibia with the ankle bone or talus and the tarsal bones. During the performance of rigorous activity, external protection of the ankle is highly advisable. Following an injury, it is mandatory.

The foot also is subject to abuse during intense physical activity. For example, during running the foot strikes the ground 800 times per mile. When landing on the ground while running, the foot absorbs a force two to three times the body weight. The foot is made up of twenty-six separate bones. These bones are held together by an incredible number of ligaments. Because the foot has so many ligaments and is subject to such abuse, it is easy to sprain. It is desirable to provide a good measure of external support to the foot and ankle in order to bind together these vulnerable bones and ligaments to prevent injury.

Ankle braces are commonly worn by people engaged in rugged activity to protect this complex structure of the foot and ankle. In sports this is important to avoid ankle sprain or to protect from preexisting injury. It is also important when engaging in other rugged activity wherein its desirable to hold the various ligaments and bones in tight conformance.

Ankle braces come in various sizes according to the size of the foot of the wearer. It is undesirable for a large ankle brace to be worn on a small foot, as it will not properly bind the bones and ligaments. A small ankle brace is likely not to fit at all on a large foot. An incorrect size of ankle brace will not promote a proper distribution of the load on the foot and ankle which is necessary to ensure each bone and ligament will bear its own stare of the load in proper fashion.

It would be desirable to have an adjustable size ankle brace in order to provide a brace of a single construction that will fit varying sizes of feet while providing the necessary protection to the ankle and foot. This permits interchanging of the brace from one user to the next. The retailer of the ankle brace need only stock a single ankle brace rather than a multiple of different sizes. This makes the ankle brace available to a greater number of athletes at an economical cost.

SUMMARY OF THE INVENTION

The invention pertains to an ankle brace of the type providing good external support to the ankle, for example like that shown in U.S. Pat. No. 4,727,863 issued Mar. 1, 1988 to Nelson. The ankle brace is adjustable in size so that it can fit a small foot as well as a large foot. The ankle brace is adjustable according to the circumference of the ankle.

The ankle brace has a base that wraps around in general conformance to the foot and ankle. An adjustable closure system is fixed to the base and adjusts on the base to accommodate ankles of varying sizes. The adjustable closure system includes a pair of mounting patches that are fixed respectively to either side of the base and are comprised of synthetic hook and loop material of the type that adheres when pressed together such as that sold under the trademark VELCRO. Movable portions of the adjustable closure assembly include detachable and movable side flaps that releasably attach on either side of the base to the respective mounting patches. Each movable flap includes an attachment tab having a surface of synthetic material corresponding to that on the mounting patch. The flap has a carrier strip that carries lace eyelets. The carrier strip is shaped in conformance with the leading edge of the normal ankle brace. The flaps are adjustable in position on the base so as to adjust the position of the eyelet carrying strips so as to regulate the enclosure size of the ankle brace when it is closed and laced.

IN THE DRAWINGS

FIG. 1 is a perspective view of an ankle brace according to the invention installed on a foot;

FIG. 2 is a side plan view of the base of the ankle brace of FIG. 1 with the side flap of the closure assembly removed and with a portion broken away for purposes of illustration;

FIG. 5 is an enlarged side elevational view of the movable side flap shown in FIG. 3 detached from the base;

FIG. 6 is a side view of the flap of FIG. 5 showing the opposite side thereof which is the side that confronts the base of the ankle brace;

FIG. 7 is a sectional view of a portion of the flap of FIG. 5 taken along the line 7—7 thereof;

DESCRIPTION OF A PREFERRED EMBODIMENT

Figure 3:
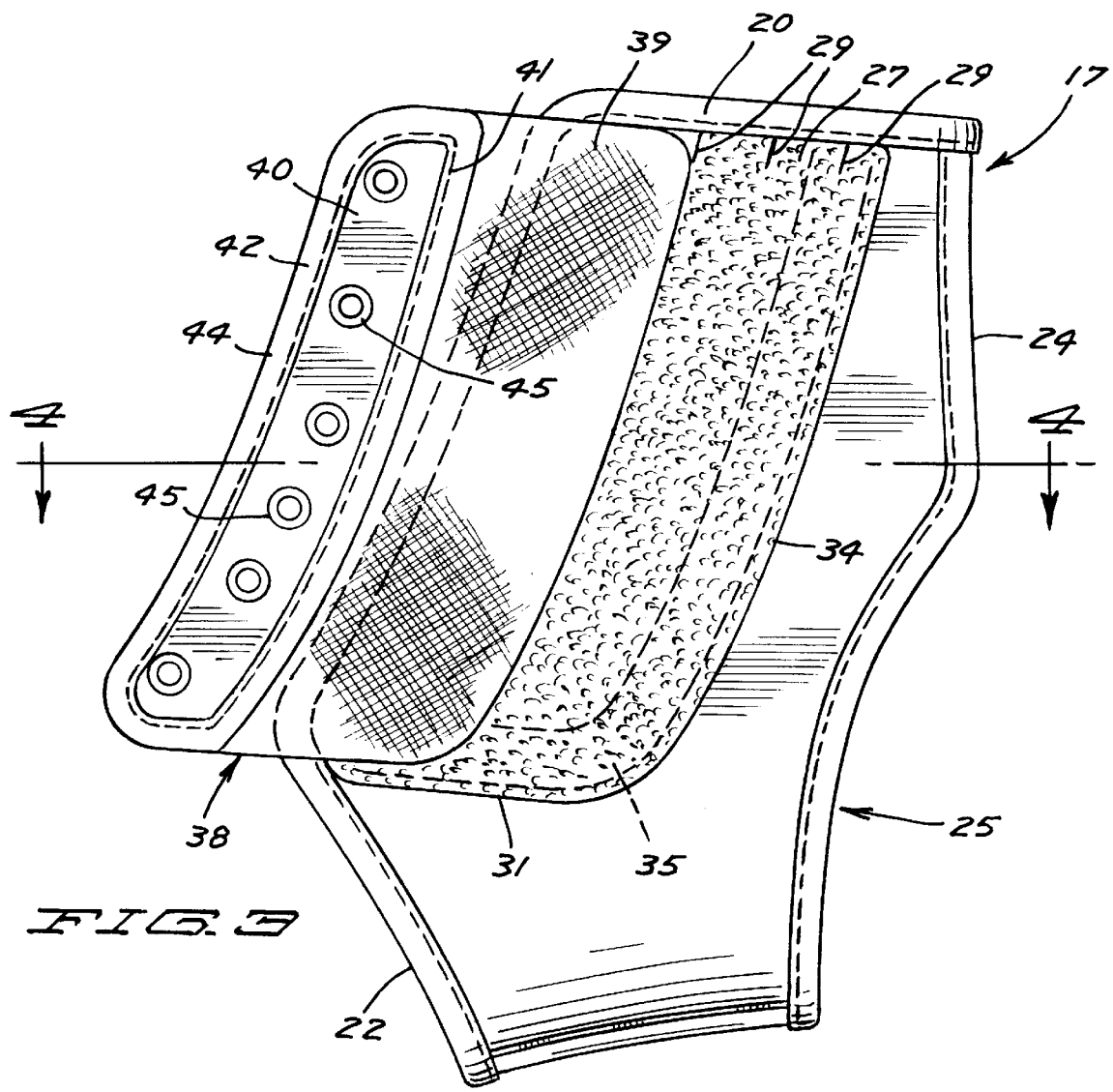
FIG. 3 is a side plan view of the ankle brace like that of FIG. 2 but showing a side flap of the closure assembly in place on the ankle brace.

Referring to FIG. 1 there is shown an ankle brace according to the invention indicated generally at 10 installed on a right foot and ankle 11 of a wearer. The foot 11 has a front toe region 12 which extends forward from the brace 10. A heal 14 extends through a heal opening of the brace. The lower leg, covered by a sock 15, extends from the top of the brace. The brace wraps around the foot and ankle in close conformance thereto. The brace has a base 17 and an adjustable closure assembly 18. The base 17 is formed of a flexible sheet material that is shaped to wrap around the rear and the lateral and medial sides of the foot and ankle extending upward along the front superior surface and beneath the sole of the foot. The closure assembly covers the front superior foot surface.

FIG. 2 is a side view of the base 17. Base 17 includes lateral and medial forward edges 21 that are curved generally in conformance with the front superior foot surface. The base 17 has a front edge 22 connected to forward edges 21. Front edge 22 wraps around the sides and bottom of the foot. The base has a heal opening 25 at the lower rear portion thereof, and a top edge 20 that wraps around the lower leg portion. When the base is positioned on a foot, the forward edges 21 are spaced apart from one another by an expanse of gap that is closed by the closure assembly. Edge binding 24 is secured to the various edges of the base.

A lateral mounting patch 27 is fixed to the lateral side of the base 17 by stitches 28. The mounting patch 27 has a leading edge 30 that is parallel to and spaced aft of the front edge 21 of the base; a lower edge 31 located near the bottom of the foot when the base is installed thereon; a top edge 32 generally parallel to upper edge 20 of the base; and a trailing edge 34 which is generally parallel to the leading edge 30 but spaced substantially rearwardly from it. Mounting patch 27 has a surface area of sufficient dimensions to encompass the region of the medial malleolus, indicated at 33 in FIG. 2. It will also cover the region of the anterior talofibular ligament in the vicinity of the malleolus. The mounting patch 27 accordingly serves as a supplementary support member reenforcing the base 17 in the vicinity of the malleolus.

The outwardly facing surface of mounting patch 27 is comprised of synthetic material of the type that adheres when pressed together, or hook and loop material of the type sold under the trademark VELCRO.

An elongate pocket 35 is formed between the mounting piece 27 and the surface of the base 17 by stitching 36. The pocket 35 extends parallel to and proximate the trailing edge 34, and curves along the bottom edge 31 a short distance. A resilient stay member 37 is located in the pocket 35. The stay member 37 is formed of a pair of interleaved helical springs that have been flattened. For example, such a stay member is shown in U.S. Pat. No. 4,727,863 issued Mar. 1, 1988 to Nelson. The stay member 37 is positioned such that it will be located rearwardly of and extend beneath the malleolus of the foot when the base is installed thereon.

Figure 4:
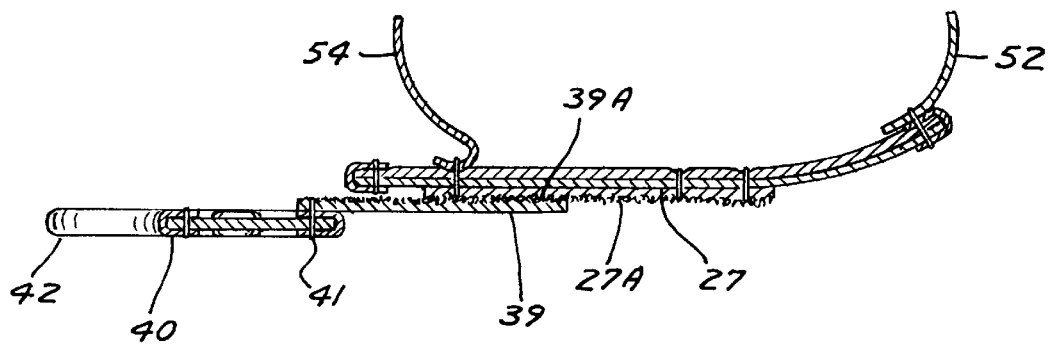
FIG. 4 is a sectional view of a portion of the ankle brace of FIG. 3 taken along the line 4—4 thereof.

FIG. 3 shows the same side of the base FIG. 2 but with a detachable movable side flap of the closure system installed thereon. A movable flap 38 includes an attachment tab 39 and a carrier strip 40. The attachment tab 39 is a sheet like member with a surface that confronts the base 17 and is formed of synthetic hook arid loop material. This surface attaches to the corresponding surface of the mounting patch 27. In FIG. 4 the sectional view of FIG. 4 the mounting patch 27 is shown as having the outwardly facing attachment surface 27A. The attachment tab 39 has a corresponding surface 39A for attachment to the patch 27. The carrier strip 40 is fixed to the front edge of the attachment tab 39 by suitable stitching 41. Stitching 41 also attaches an edge binding 42 along the edges of the carrier strip 40. The attachment tab 39 and the carrier strip 40 correspond in length from top to bottom with the mounting patch 27. The carrier strip 40 has a front edge 44 that is curved to conform to the front superior foot surface and corresponds to the usual forward edge of an ankle brace like that shown in the aforementioned U.S. Pat. 4,727,863. The carrier strip 40 carries a plurality of lace eyelets 45. The lace eyelets 45 are bunched together in the vicinity that covers the middle superior foot surface.

The position of the movable flap 38 is adjustable on the base 17 with respect to the patch 27. The flap 38 is simply pulled away from a position of attachment with the mounting patch 27 and moved. The flap 38 is moved fore or aft according to the size of the foot to be fitted. The flap 38 is readily detached from the base 17 by pulling it away and disengaging the hook and loop type attaching materials.

The flap is located according to the size of the foot. The base can have graduation indicia for placement of the flap according to foot size, for example small, medium and large. Indicia 29 are shown on the base 17 in FIG. 2. The top part of the trailing edge of the movable member can be positioned next to one of the indicia 29 for small, medium and large size adjustment. Generally in any case the flap will still cover the area 33 of the malleolus.

Flap 38 is better shown in FIGS. 5 and 6. The carrier strip 40 can be formed of a suitable strong material such as vinyl. The wide expanse of the attachment tab 39 provides a wide surface 39A for secure attachment to the mounting patch 27. The attachment of the carrier strip 40 to the attachment tab 39 is clearly shown in FIG. 7.

Figure 8:
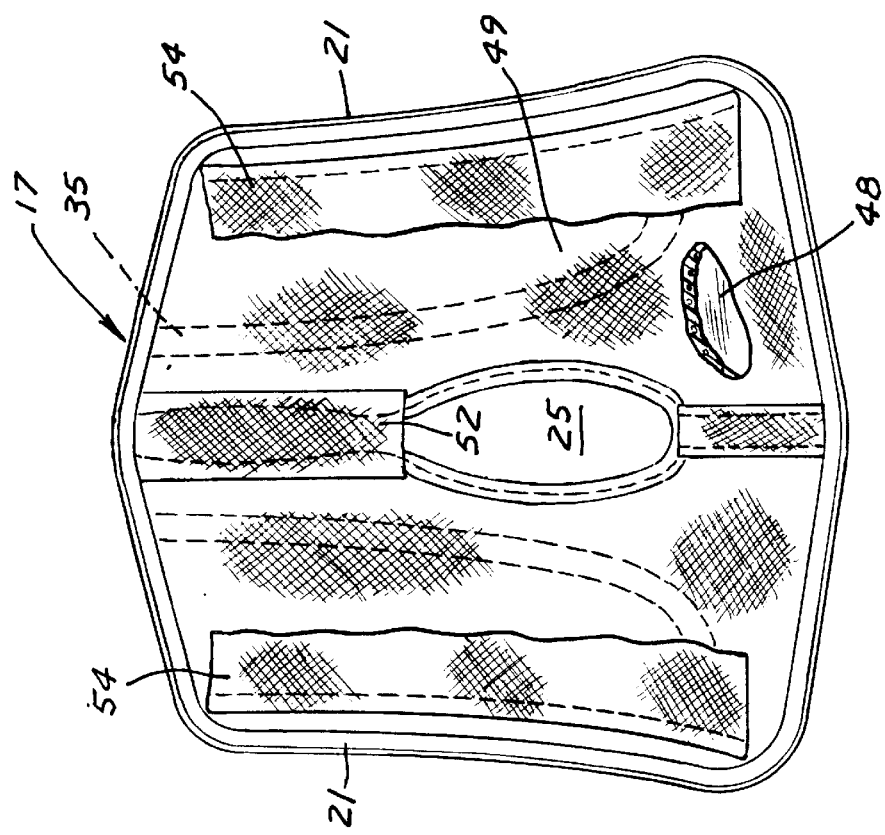
FIG. 8 is a front view of the base of the ankle brace of the invention in a spread open position with portions removed for purposes of illustration.

FIG. 8 shows the inside of the base. The outer surface of the base is a sheet like outer layer 48 of inelastic material such as vinyl. A liner 49 is fixed to the inside surface of the outer layer 48. Rear edges 50 of the outer layer 48 are connected by a stretchable elastic rear member 52.

A tongue is fixed to forward edges of the base 17 on the inside thereof. Tongue 54 is fastened at either side to the inner portions of the base. The tongue 54 is elastic and stretches across the foot with the base installed thereon, as shown in FIG. 1.

Figure 9:
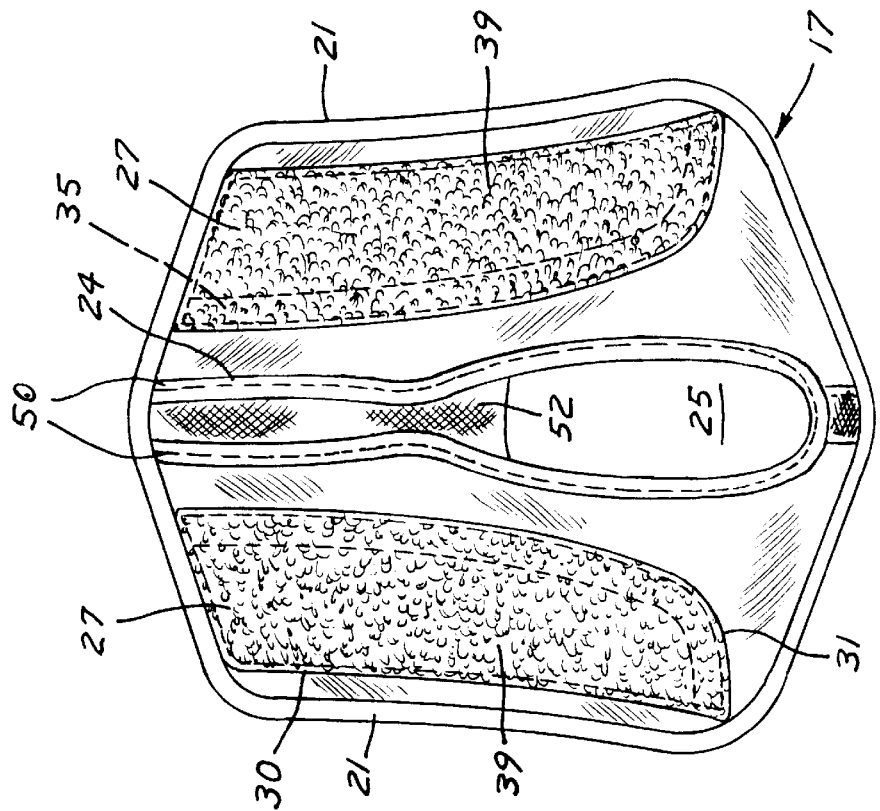
FIG. 9 is a back view of the base of the ankle brace of FIG. 8 shown without the flaps.

FIGS. 8 and 9 show that the lateral and medial sides of the brace are symmetrical. The base has lateral and medial mounting patches 27 located symmetrically thereon. Movable lateral and medial flaps 38 attach to either side of the base. Each flap has a carrier strip 40 with lace eyelets 45. As shown in FIG. 1, the lace eyelets carry a common lace 56.

In use the base is installed on a foot. The flaps 38 are applied to the base 17 with a suitable distance between the respective front, eyelet carrying edges. The flaps adhere securely to the base. The lace can then be tightened in order to achieve the usual, desirable ankle brace support.

It is claimed:

1. An adjustable size ankle brace, comprising:
a base of flexible material shaped to wrap around the rear and sides of a foot and ankle;
a first removable flap for releasable connection to a first side of the base, and a second removable flap for releasable connection to a second side of the base;
first attachment means for attachment of the first removable flap to the first side of the base, and second attachment means for attachment of the second removable flap to the second side of the base;
said first flap carrying a first eyelet strip having a set of lace eyelets, and second flap carrying a second eyelet strip having a set of lace eyelets;
a lace trained between the eyelets on the first and second eyelet strips;
whereby the positioning of the side flaps on the base is adjustable by removing the flaps from the base and repositioning them on the base according to the size of the foot of the intended wearer of the brace.

2. The ankle brace of claim 1 wherein:
each flap has an attachment tab for attachment to the side of the brace, and an eyelet carrier strip connected to the tab.

3. The ankle brace of claim 2 wherein:
means for attachment of the flaps to the sides of the base includes first and second mounting patches fixed to respective sides of the base and formed of hook and loop type synthetic material, said tabs of the flaps having corresponding hook and loop type material for releasable attachment to the mounting patches.

4. The ankle brace of claim 3 wherein:
the mounting patches are positioned on the base and of sufficient dimensions to encompass the malleolus when the base is installed on a foot and ankle.

5. The ankle brace of claim 4 wherein:
the tabs of the flaps are of sufficient dimensions to encompass the malleolus when the base is installed on a foot.

6. The ankle brace of claim 5 wherein:

the carrier strips are slightly curved in conformance with the curvature of the front superior surface of the foot and ankle.

7. The ankle brace of claim 6 including:

graduation indicia on the base for guidance in placement of the flaps according to the foot size of the intended wearer of the brace.

8. The ankle brace of claim 7 wherein:

the base extends beneath the sole of the foot.

9. The ankle brace of claim 8 including:

elongate pockets on either side of the base located behind the malleolus, and a resilient stay member located in each pocket.

10. An adjustable size ankle brace comprising:

a base of flexible sheet material shaped to encompass the ankle and the rear and lateral and medial sides of the foot, having lateral and medial sides and lateral and medial forward edges that come toward one another over the front superior ankle and foot region with a gap between them;

an adjustable closure assembly closing the gap between the lateral and medial forward edges of the bases to secure the brace to the foot and ankle;

said adjustable closure assembly including a lateral flap and a medial flap, each flap having an attachment tab and an eyelet carrier strip connected to the attachment tab;

each eyelet carrier strip having a plurality of lace eyelets;

a lace trained between the lace eyelets of the carrier strips;

a medial mounting patch fixed to the medial side of the base;

a lateral mounting patch fixed to the lateral side of the base; and releasable attachment means on the attachment tabs and mounting patches for releasable attachment of the lateral and medial flaps respectively to the lateral and medial mounting patches whereby the size of the ankle brace is variable according to positioning of the flaps on the mounting patches.

11. The ankle brace of claim 10 wherein:

the attachment means for releasable attachment of the flaps and mounting patches comprises hook and loop type synthetic fastening material.

12. The ankle brace of claim 11 including:

an elastic tongue connecting the lateral and medial forward edges of the base.

13. The ankle brace of claim 11 wherein:

the mounting patches are positioned on the base and of sufficient dimensions to encompass the lateral and medial malleolus when the base is installed on an ankle and foot.

14. The ankle brace of claim 13 wherein:

the tabs of the flaps are of sufficient dimensions to encompass the lateral and medial malleolus when the base is installed on a foot and ankle and the flaps are installed on the base.

15. The ankle brace of claim 14 wherein:

the carrier strips are slightly curved in conformance with the curvature of the front superior surface of the foot and ankle.

16. The ankle brace of claim 15 including:

graduation indicia on the base for guidance in placement of the flaps according to the foot size of the intended wearer of the brace.

17. The ankle brace of claim 16 wherein:

each mounting patch has a leading edge that is parallel to and spaced aft of the respective front edge of the base and forward of the malleolus, a trailing edge that is generally parallel to the leading edge and located aft of the malleolus, each mounting patch generally corresponding in height to the distance between the top edge of the base and the sole of the foot.

* * * * *

UNITED STATES PATENT AND TRADEMARK OFFICE
CERTIFICATE OF CORRECTION

PATENT NO.    : 5,814,002
DATED         : September 29, 1998
INVENTOR(S)   : Ronald E. Nelson It is certified that error appears in the above-identified patent and that said Letters Patent is hereby corrected as shown below:

Column 1,
Line 2, after the title and before the "BACKGROUND OF THE INVENTION" insert the following:

-- CROSS-REFERENCE TO RELATED APPLICATION

This application claims priority from provisional application No. 60/031,304, filed November 19, 1996, the disclosure of which is incorporated by reference. --

Signed and Sealed this

Ninth Day of September, 2003

JAMES E. ROGAN
*Director of the United States Patent and Trademark Office*